(12) United States Patent
Poddar

(10) Patent No.: US 10,537,493 B2
(45) Date of Patent: Jan. 21, 2020

(54) TRAVEL PACKAGING FOR MEDICATIONS

(71) Applicant: Satish Poddar, Duluth, GA (US)

(72) Inventor: Satish Poddar, Duluth, GA (US)

(*) Notice: Subject to any disclaimer, the term of this patent is extended or adjusted under 35 U.S.C. 154(b) by 0 days.

(21) Appl. No.: 15/659,278

(22) Filed: Jul. 25, 2017

(65) Prior Publication Data
US 2017/0319434 A1    Nov. 9, 2017

Related U.S. Application Data

(63) Continuation-in-part of application No. 14/926,068, filed on Oct. 29, 2015, now abandoned.

(51) Int. Cl.
| | |
|---|---|
| *B65D 83/04* | (2006.01) |
| *B65D 85/42* | (2006.01) |
| *A61J 1/03* | (2006.01) |
| *B65B 7/16* | (2006.01) |
| *B65D 75/36* | (2006.01) |
| *B65D 75/54* | (2006.01) |
| *B65B 5/04* | (2006.01) |
| *G16H 20/13* | (2018.01) |

(52) U.S. Cl.
CPC ............. *A61J 1/035* (2013.01); *B65B 5/04* (2013.01); *B65B 7/16* (2013.01); *B65D 75/367* (2013.01); *B65D 75/54* (2013.01); *G16H 20/13* (2018.01); *A61J 2205/30* (2013.01); *B65B 2220/14* (2013.01); *B65B 2230/02* (2013.01); *B65D 2203/12* (2013.01)

(58) Field of Classification Search
CPC ......... A61J 1/035; A61J 2205/30; B65B 5/06; B65B 7/16; B65B 5/04; B65D 75/367; B65D 75/54; B65D 83/04

USPC .............. 206/459.5, 539, 534, 532, 530
See application file for complete search history.

(56) References Cited

U.S. PATENT DOCUMENTS

| 8,020,702 B2 | 9/2011 | Strub et al. | |
|---|---|---|---|
| 8,905,237 B2 | 12/2014 | Alonso et al. | |
| 2003/0087848 A1* | 5/2003 | Bratzler | A61K 31/138 |
| | | | 514/44 A |
| 2005/0150806 A1* | 7/2005 | Lorenzato | A61J 7/04 |
| | | | 206/534 |
| 2006/0144749 A1* | 7/2006 | Arnold | A61J 1/035 |
| | | | 206/538 |

(Continued)

OTHER PUBLICATIONS

Apple Valley Pharmacy, "Our Custom Pill Packaging Makes Complicated Regimens and Remembering to Take Medications a Little Easier", © 2014, http://applevalleypharmacy.com/pill-packing-hudson-valley[orange-country-warwick-ny/,1 page.

*Primary Examiner* — Rafael A Ortiz
(74) *Attorney, Agent, or Firm* — BakerHostetler

(57) ABSTRACT

The present disclosure provides a medication package. The medication package may include a first medication stored in a first cavity and a second medication stored in a second cavity. The first medication may be selected, based on a geographical region, from a group of classes of medications. The second medication may be selected, based on the geographical region, from a group of classes of medications, wherein the class of the second medication is different than that of the first medication. The geographical region may be a contiguous region and may be defined by a common attribute.

20 Claims, 9 Drawing Sheets

(56) References Cited

U.S. PATENT DOCUMENTS

| | | | |
|---|---|---|---|
| 2008/0277307 A1* | 11/2008 | Mazur | A61J 7/0481 |
| | | | 206/534 |
| 2015/0209227 A1 | 7/2015 | Bamberger | |
| 2016/0022542 A1* | 1/2016 | Lehmann | G06F 19/3462 |
| | | | 206/534 |
| 2016/0143807 A1* | 5/2016 | Ika | A61J 1/03 |
| | | | 206/216 |
| 2016/0147976 A1* | 5/2016 | Jain | A61J 1/035 |
| | | | 705/2 |

* cited by examiner

TRAVEL PACKAGING FOR MEDICATIONS

CROSS REFERENCE TO RELATED APPLICATIONS

This application is a continuation-in-part of, and claims priority to, U.S. patent application Ser. No. 14/926,068, filed Oct. 29, 2015. U.S. patent application Ser. No. 14/926,068 is entitled "Travel Packaging For Medications" and is incorporated by reference herein in its entirety.

TECHNICAL FIELD

The technical field relates generally to medication packaging and more particularly to travel packaging for medications.

BACKGROUND

Many people enjoying travelling to other parts of the world to see new sights and enjoy the local culture. Similarly, the modern business world requires many workers to travel abroad to investigate a potential new market or meet a foreign client, for example. Visiting a new locale, however, may expose a traveler to novel circumstances or environments which may adversely affect the traveler's health. For instance, the water purification technology used at a travel destination may be less advanced than that of a traveler's home city. When the traveler drinks the water at the travel destination, the traveler may be exposed to bacteria, parasites, or other pathogens that the traveler's immune system is unaccustomed to handling. As another example, certain diseases, such as malaria, may be common in some regions of the world. When a traveler visits one of those regions, the traveler may be exposed to those diseases to which the traveler might not have otherwise been exposed. It is not uncommon for a particular travel destination to be associated with several such factors that may each adversely affect a traveler's health. Moreover, even ailments common in a traveler's home country may strike when at a travel destination.

In order to allow a traveler to respond, while on the trip, to such adverse health conditions caused by various aspects of a travel destination, a health care provider may supply a medication for each of the potential health conditions. The traveler may carry each of the separate medications with him or her to the travel destination. Carrying each of the medications in separate packaging, such as in separate bottles or blister packs, may prove cumbersome and space-consuming for the traveler, however.

SUMMARY

Disclosed herein is a medication package and methods of assembling a medication package. In one aspect, a medication package may comprise a first cavity and a second cavity, which may be physically connected to the first cavity. A first medication may be sealed in the first cavity and a second medication may be sealed in the second cavity. A seal of the first cavity must be broken to access the first medication and a seal of the second cavity must be broken to access the second medication. The first medication may be selected, based on a geographic region, from a first plurality of medications. Each medication of the first plurality of medications may belong to a first class of medications selected from a group consisting of: anti-allergy, anti-diarrhea, anti-emetic, anti-spasmodic, antibiotic, antiviral, anti-parasitic anti-fungal, non-steroidal pain reliever, narcotic pain reliever, anti-anxiety, hypnotic, antitussive, antacid, and anti-motion sickness. The second medication may be selected, based on the geographic region, from a second plurality of medications. Each medication of the second plurality of medications may belong to a second class of medications, different from the first class of medications, and selected from the group consisting of: anti-allergy, anti-diarrhea, anti-emetic, anti-spasmodic, antibiotic, antiviral, anti-parasitic anti-fungal, non-steroidal pain reliever, narcotic pain reliever, anti-anxiety, hypnotic, antitussive, antacid, and anti-motion sickness.

In another aspect, a method of assembling a mediation package may include determining a first medication based on a geographical region. The first medication may be selected from a first plurality of medications. Each medication of the first plurality of medications may belong to a first class of medications selected from a group consisting of: anti-allergy, anti-diarrhea, anti-emetic, anti-spasmodic, antibiotic, antiviral, anti-parasitic anti-fungal, non-steroidal pain reliever, narcotic pain reliever, anti-anxiety, hypnotic, antitussive, antacid, and anti-motion sickness. The second medication may be determined based on the geographical region. The second medication may be selected from a second plurality of medications. Each medication of the second plurality of medications may belong to a second class of medications selected from the group consisting of: anti-allergy, anti-diarrhea, anti-emetic, anti-spasmodic, antibiotic, antiviral, anti-parasitic anti-fungal, non-steroidal pain reliever, narcotic pain reliever, anti-anxiety, hypnotic, antitussive, antacid, and anti-motion sickness. The first medication may be disposed within a first cavity of the medication package and the second medication may be disposed within a second cavity of the medication package. The first cavity and the second cavity may be connected to one another via, at the least, the medication package.

In another aspect, a substrate may be provided and a travel destination may be received. First and second medical products each may be determined based on the travel destination. A substrate requirement may be determined that is associated with at least one of the first medical product and the second medical product. The substrate may be modified based on the substrate requirement. The first and second medical products each may be disposed in physical connection with the substrate.

BRIEF DESCRIPTION OF THE DRAWINGS

The following detailed description is better understood when read in conjunction with the appended drawings. For the purposes of illustration, examples are shown in the drawings; however, the subject matter is not limited to the specific elements and instrumentalities disclosed. In the drawings.

DETAILED DESCRIPTION OF ILLUSTRATIVE EMBODIMENTS

Described herein is travel packaging for medications that may provide a convenient, all-in-one package for all or many of the medications or other medical products that are anticipated to be needed by a patient while on a trip. The package may be provided by a health care provider, such as a pharmacist or physician, to a patient in preparation for a trip by the patient to a particular travel destination. The package may include one or more medications or other medical products. One or more of the medications or other medical products included in the package may be determined by the health care provider according to the travel destination. For example, a medication for the treatment of malaria may be included in the package on the basis of the travel destination being a certain tropical region in which malaria is prevalent. The package may then be taken by the patient on his or her trip to the travel destination wherein the medical products may be used, if needed.

In describing embodiments of the present disclosure illustrated in the figures, specific terminology is employed for the sake of clarity. The disclosure, however, is not intended to be limited to the specific terminology so selected, and it is to be understood that each specific element includes all technical equivalents that operate in a similar manner to accomplish a similar purpose.

Figure 1:
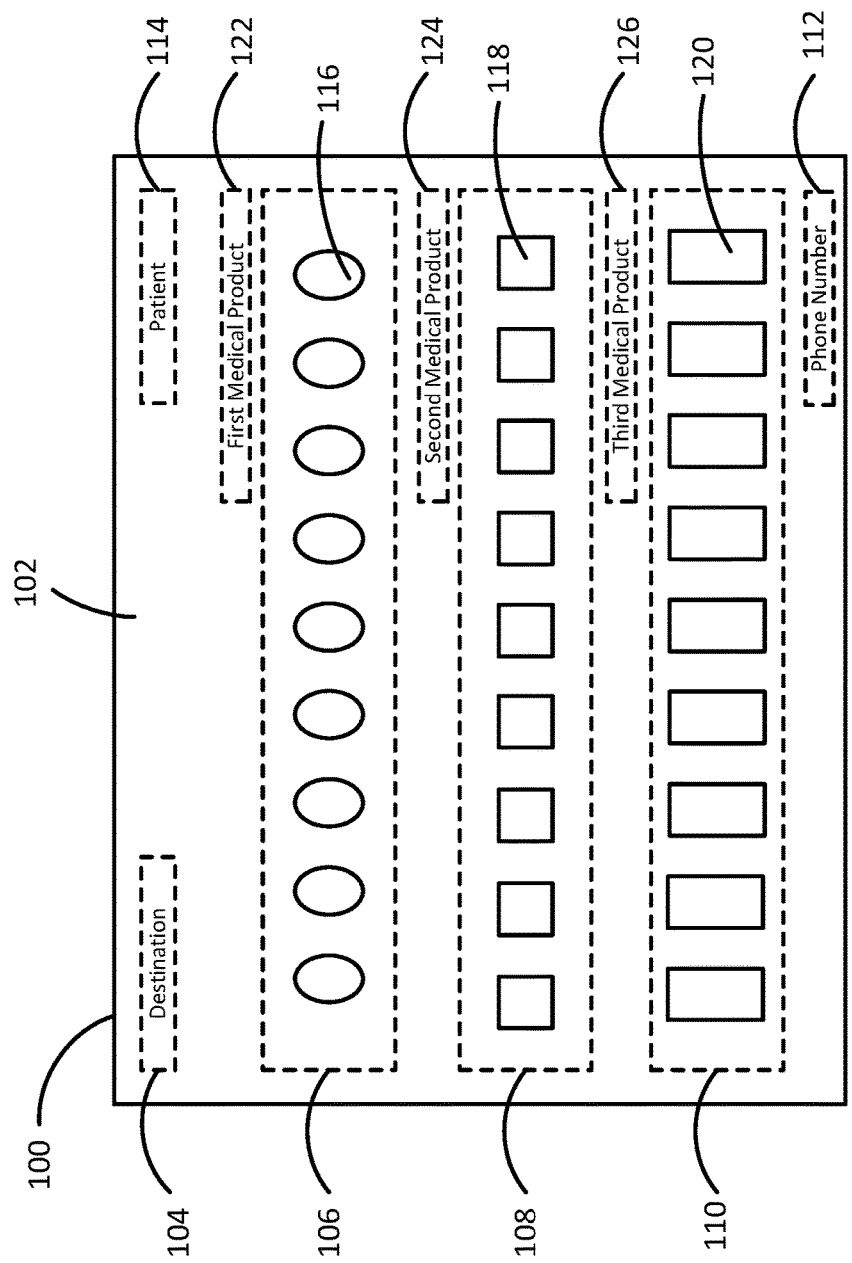
FIG. 1 illustrates a front view of an exemplary travel package for medications or other medical products.

FIG. 1 depicts a front view of an exemplary embodiment of a package 100 for one or more medical products. As used herein, the term "medical product" may refer to a pharmaceutical drug (e.g., an ingestible pill, an ingestible liquid solution, a topical cream or ointment, an ear drop, an eye drop, an inhalant, etc.) or a medical device (e.g., a bandage, a swab, medical gloves, a scalpel, forceps, etc.). The medical product may be a prescription medical product or an over-the-counter medical product.

The package 100 may be embodied as a blister package, such as depicted in FIG. 1, configured to securely contain one or more medical products. The package 100 may include a substrate 102, such as cardboard or plastic, defining a plurality of sealed blister cavities in which each cavity may secure a dose (e.g., a pill) of a medical product and be individually sealed such that the seal is broken to access the medical product. The backing of each cavity may be comprised of a thin material, such as foil, through which the medical product in the cavity may be pushed by the user to expel the medical product from the package 100.

In an aspect, each of the sealed blister cavities may be sterile. The cavities containing the medical products may be arranged in one or more regions, such as a first region 106, a second region 108, and a third region 110. The medical product contained in each region may be a different medical product from the medical products contained in the other regions. For example, the first region 106 may include a first medical product 116, the second region 108 may include a second medical product 118, and the third region 110 may include a third medical product 120. For sake of visual clarity, not all of the first medical product 116, the second medical product 118, and the third medical product 120 are labeled in FIG. 1. The package 100 may include a label identifying the medical product disposed within a certain region. For example, the package 100 may include a first medical product label 122 identifying the first medical product 116 in the first region 106, a second medical product label 124 identifying the second medical product 118 in the second region 108, and a third medical product label 126 identifying the third medical product 120 in the third region 110. In an aspect, the medical products, such as the first medical product 116, the second medical product 118, and/or the third medical product 120, may each have an identical or nearly identical expiration date, thus preventing a situation in which one of the medical products is expired while one or more of the other medical products are not expired.

The medical products included in the package 100, such as the first medical product 116, the second medical product 118, or the third medical product 120, may each be determined according to a travel destination (e.g., a city, country, continent, or region), such as a travel destination contemplated by the patient. In particular, the medical products may be determined based on one or more factors associated with the travel destination. A factor associated with the travel destination may include an infrastructure factor, an environmental factor, a flora/fauna factor, a travel factor, or a common disease factor.

An infrastructure factor may refer to any aspect of the travel destination's infrastructure which may cause or contribute to an adverse health effect in the patient. For example, an infrastructure factor may include an indication that the water treatment system of the travel destination has a lesser or different degree of efficacy compared to that of the locale from which a patient is traveling. To illustrate, a patient traveling to a less developed country with poor or no water treatment facilities may suffer from diarrhea caused by pathogens in the water supply. An infrastructure factor may further relate to the sewer system in place at the travel destination. For instance, if the travel destination has only an open sewer system with no sewer treatment facilities, this may put a patient at increased risk of waste-borne illnesses.

An environmental factor may refer to any aspect of the travel destination's environment that may cause or contribute to an adverse health effect in the patient. As one example, an environmental factor may indicate that the travel destination suffers from severe air pollution. The air pollution may, for example, exasperate an asthma condition of the patient or put the patient at increased risk of respiratory distress or infection. An environmental factor may include an indication of a weather condition of the travel destination. For instance, an environmental factor may include an indication that the sun is particularly intense at the travel destination and, therefore, the patient may be easily sunburned. As another example, an environmental factor may indicate that the travel destination is particularly hot or cold. As yet another example, the environmental factor may include an indication that the travel destination contains certain allergens.

A flora/fauna factor may include an aspect of the travel destination pertaining to a macroscopic plant or animal within the travel destination that may harm the patient. For examples, a flora/fauna factor may include an indication that the travel destination is host to jellyfish, mosquitoes or other biting insects, or venomous snakes. A flora/fauna factor may further include an indication of an animal that may cause a parasitic invasion of the patient's body, such as guinea worms, intestinal worms, or botflies. As yet another example, a flora/fauna factor may include an indication that the travel destination has poison ivy.

A travel factor may refer to any aspect of the act of traveling, such as to the travel destination, that may cause or contribute to an adverse health effect of the patient. The travel factor may include an indication of a mode of travel, such by car, ship, airplane, or train. For example, traveling on an ocean-going ship may cause some individuals to experience the nausea and dizziness associated with seasickness. Further, the travel factor may include an indication that an individual is exposed to a high concentration of other people in a confined space, such as in a train or airplane, which may increase the individual's chances of contracting a communicable disease, such as sinusitis or pharyngitis. The travel factor may include an indication that an individual is at an increased risk of dehydration due to traveling. The dehydration may, in turn, put the individual at an increased risk of other conditions or diseases, such as a urinary tract infection.

A common disease factor may refer to an aspect of the travel destination relating to a disease, illness, condition, etc., that commonly affects individuals at the travel destination. For example, certain diseases, such as malaria or dengue fever, may be prevalent in tropical or subtropical regions throughout the world. Others, such as chagas disease, may be prevalent in the tropical or subtropics regions of Central and South America.

It will be appreciated that the medical products included in the package 100 may include not only those medical products that directly treat a condition caused by or otherwise related to one of the aforementioned factors, but may also include medical products that treat secondary effects of the condition or provide supportive treatment. For example, if the patient is traveling to a region in which malaria is common, the package 100 may include not only an antimalarial medication but also a medication to reduce fever and/or a medication to relieve pain. In some aspects, the medical products included in the package 100 may include medical products corresponding to a partial treatment for a particular disease or medical condition, or symptom thereof. For example, the package 100 may include a number of pills comprising a half-dose of the medical product. This may provide temporary relief or treatment to the patient until the patient can locate a health care provider at the travel destination, while still allowing the package 100 to remain compact due to the inclusion of only the partial dosage instead of a full dosage.

The medical products included in the package 100, such as the first medical product 116, the second medical product 118, or the third medical product 120, may additionally be based on the individual medical needs of the patient. This may include a consideration of the medical needs of the patient notwithstanding the patient's travel or the travel destination, such as a medical product that the patient is already taking before the trip. For example, a patient may suffer from high-blood pressure, in which case the package 100 may include the patient's usual blood pressure medication along with other medical products determined according to the travel destination. The individual medical needs of the patient may also include those medical needs which may address conditions commonly experienced by the patient, but which the patient does not already suffer from and are unrelated to the travel destination. For example, the package 100 may include a medical product that treats a common cold, a sinus infection, acid reflux, urinary tract infection, or minor pains. In this manner, the patient may be provided with a single, convenient travel package that may fulfill the patient's medical needs—both known and contemplated—while the patient is traveling.

The package 100 may further include a destination label 104 indicating the travel destination according to which one or more of the medical products has been determined. The package 100 may also include a patient label 114 indicating the patient for whom the package is prepared. The package 100 may include a phone number 112. The phone number 112 may correspond with a medical help line in which the patient may solicit directions or information concerning the medical products and the conditions that the medical products may address. The package 100 may include a website address (e.g., a uniform resource locator (URL)) pointing to a website at which the patient may receive information concerning the medical condition afflicting the patient or the medical products. In an aspect, the website may facilitate a real-time consultation with a health care provider (a "virtual visit").

Figure 2:
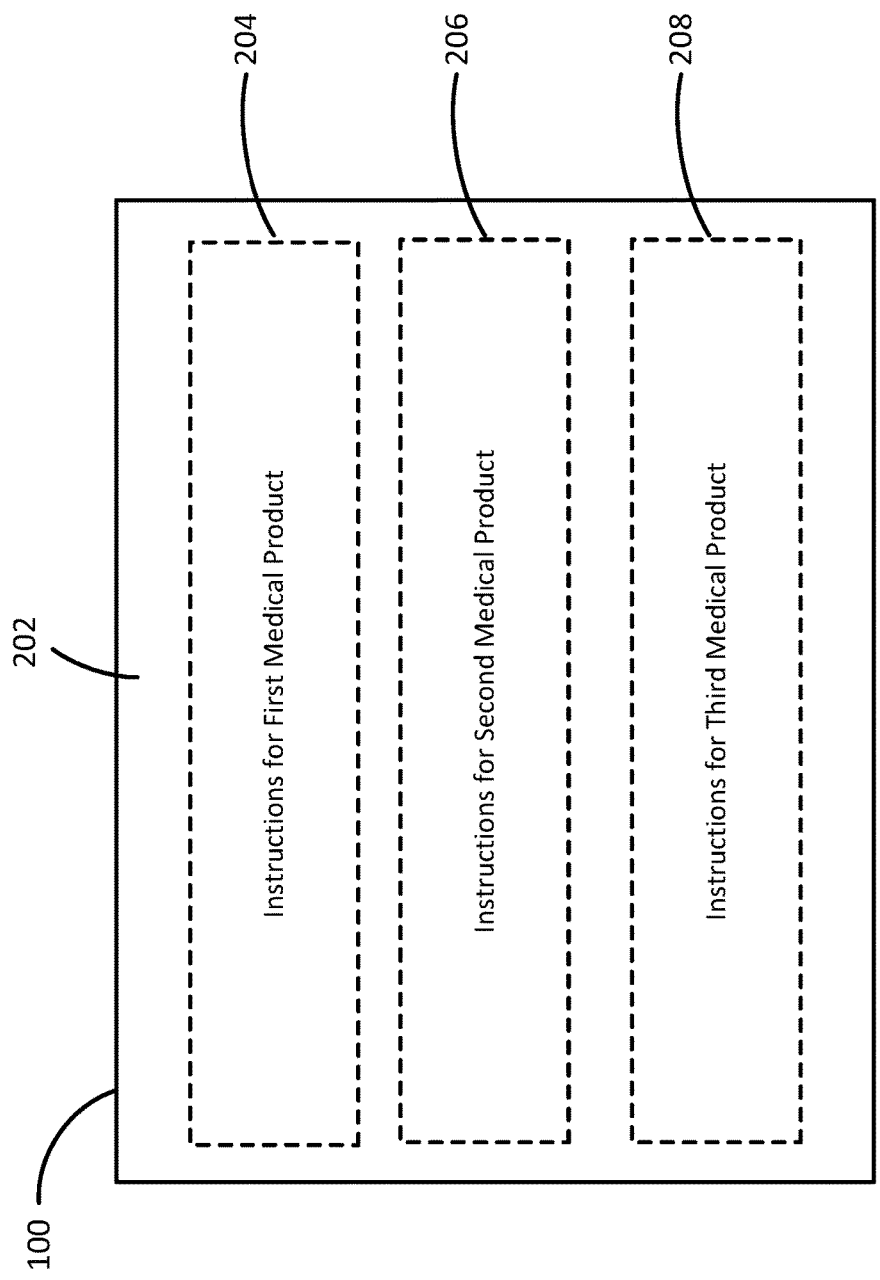
FIG. 2 illustrates a rear view of an exemplary travel package for medications or other medical products.

FIG. 2 depicts a rear view of the package 100. The package 100 may include one or more instruction regions in which instructions (e.g. dosage information) or other information (e.g., medical conditions or symptoms that the medical product addresses or side effects of the medical product) about the medical products may be provided. Additionally or alternatively, each instruction region may include the name or another identifier of the corresponding medical product. Each instruction region may correspond with one of the medical products included in the package 100. For example, a first instruction region 204 may correspond with the first medical product 116, a second instruction region 206 may correspond with the second medical product 118, and the third instruction region 208 may correspond with the third medical product 120.

Figure 3:
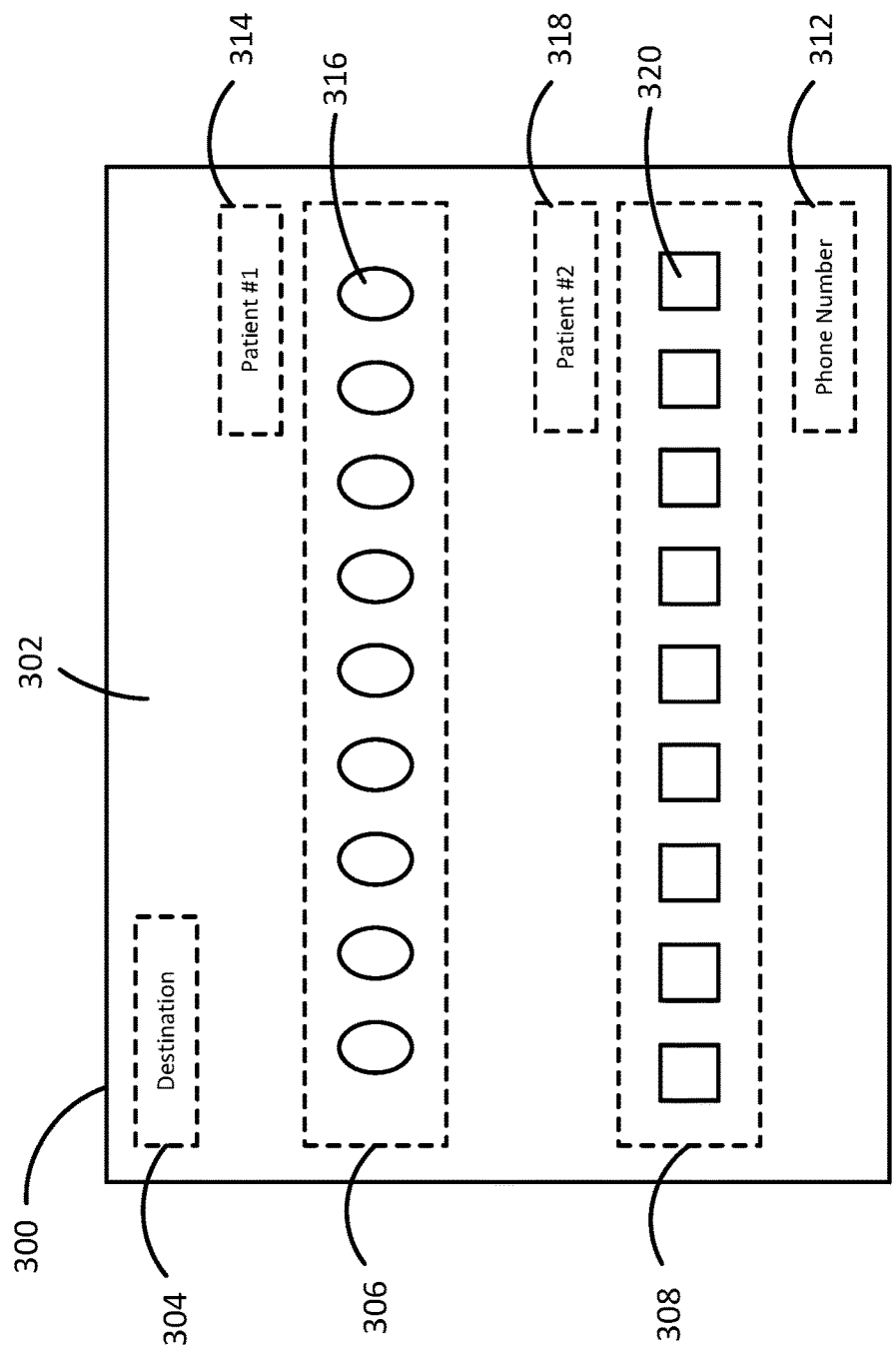
FIG. 3 illustrates a front view of an exemplary travel package for medications or other medical products.

FIG. 3 depicts an alternative embodiment in which a package 300 may include medical products intended for use by more than one patient, such as a family of patients. Like the package 100 depicted in FIG. 1, the package 300 may be embodied as a blister pack including a substrate 302 defining a plurality of sealed blister cavities. Each cavity may secure a dose (e.g., a pill) of a medical product. The cavities may be arranged in one or more regions, such as a first region 306 and a second region 308. Each region may be associated with a different patient (e.g., the medical product contained in a region are intended for use by a particular patient) and labeled as such. For instance, the first region 306 may be associated with a first patient and a first patient label 314 identifying the first patient may be positioned on the package 300 proximate to the first region 306. The second region 308 may be associated with a second patient and a second patient label 318 may be positioned on the package 300 proximate to the second region 308.

The medical products, such as a first medical product 316 disposed with the first region 306 and a second medical product 320 disposed within the second region 308, intended for the patients may be different medical products or the same medical product but in different dosages. The medical products included in the package 300 may be determined according to the factors described herein, but also according to the number of patients and their individual attributes, such as age, sex, and weight. As an example of an embodiment of the package 300 in which the medical products are the same medical product in different dosages, the first patient and the second patient may intend to go on a trip to a country that has poor water sanitation that may be likely to cause diarrhea. Accordingly, the package 300 may include an anti-diarrhea medication, such as loperamide, as the first medical product 316 and the second medical product 320. Since the first patient may weigh more than the second patient, each loperamide pill of the first medical product 316 may be in a higher dose than those of the second medical product 320.

The package 300 may include a destination label 304 indicating the travel destination according to which one or more of the medical products may be determined. The package 300 may further include a phone number 312 corresponding to a medical help line. The package 300 may include a website address (e.g., a URL) to a website at which the patient may receive information about the medical products or medical conditions or engage in a real-time consultation with a health care provider (a "virtual visit"). Alternatively, a single dimensional or multi-dimensional barcode or other scannable indicia may be provided on the package to be scanned by a smart phone or other device to access relevant information. The package may include multiple barcodes or other scannable indicia for each type of product or for each dose such that a traveler may scan the index prior to breaking the seal of any individual cavity. The information from the scan may then be stored in the smart phone or other device for later retrieval so that the patient and the health care professional can audit the types and amounts of medical products accessed and consumed. Alternatively, the smart phone or other device may communicate such information to a website or other server to be accessed by the traveler or a physician in either real time or at a later date. A questionnaire associated with the scanned indicia may be completed by the traveler to facilitate the virtual visit. Such tracking will assist the health care professional to monitor the traveler for progress and enable the health care professional to change the prescription or dosage as part of follow-up virtual visits during the course of travel. Such scannable index may, for example, be a 2-D barcode readable by a handheld scanner or smart phone application used for other technologies as is known by those skilled in the art.

Figure 4:
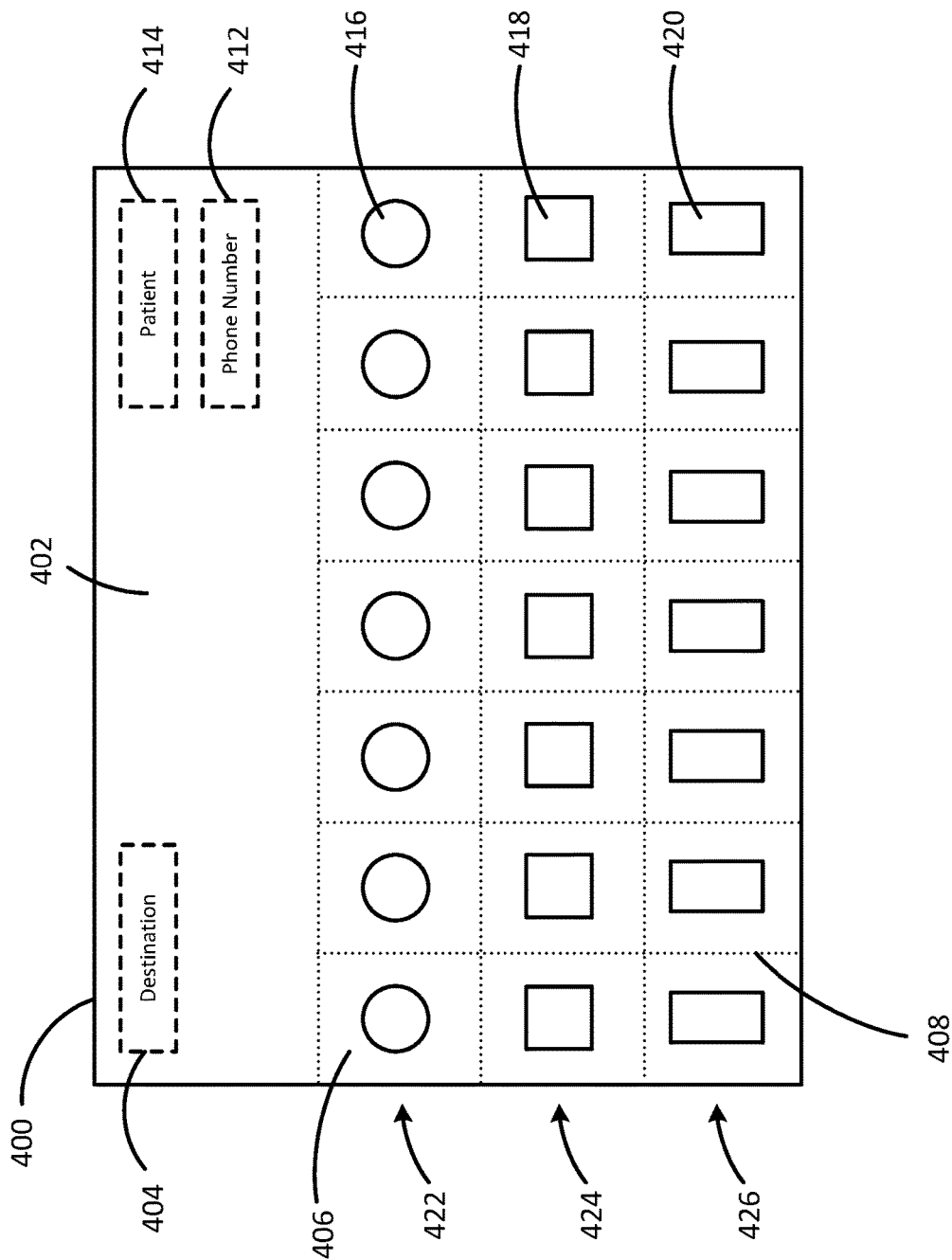
FIG. 4 illustrates a front view of an exemplary travel package for medications or other medical products.

FIG. 4 depicts another alternative embodiment in which a package 400 may include a perforated sheet 402 comprising a plurality of packets 406. Each of the packets 406 may be defined by a perforated edge 408 and connected via at least one perforated edge 408 with at least one other packet 406. Each of the packets 406 may contain a pill or other dosage of a medical product. Each packet 406 may include a top layer peripherally adhered to a bottom layer to form a sealed cavity between the top layer and the bottom layer. The top and bottom layers may be composed of paper, thin plastic, foil, or a combination thereof. In use, one of the packets 406 may be separated from the package 400 along its perforated edge(s) 408, and the packet 406 may be ripped open. Alternatively, the bottom and top layers may be peeled apart to allow access to the pill or other form of the medical product contained therein.

The packets 406 may be arranged according to the medical product contained therein. For example, a dose (e.g. a pill) of a first medical product 416 may be contained in each of the packets 406 in a first row 422 of the package 400, a dose of a second medical product 418 may be contained in each of the packets 406 of a second row 424 of the package 400, and a dose of a third medical product 420 may be contained in each of the packets 406 of a third row 426 of the package 400.

The package 400 may include a destination label 404 indicating the travel destination according to which one or more of the medical products may be determined. The package 400 may further include a patient label 414 identifying the patient or a phone number 412 corresponding to a medical help line.

Figure 5:
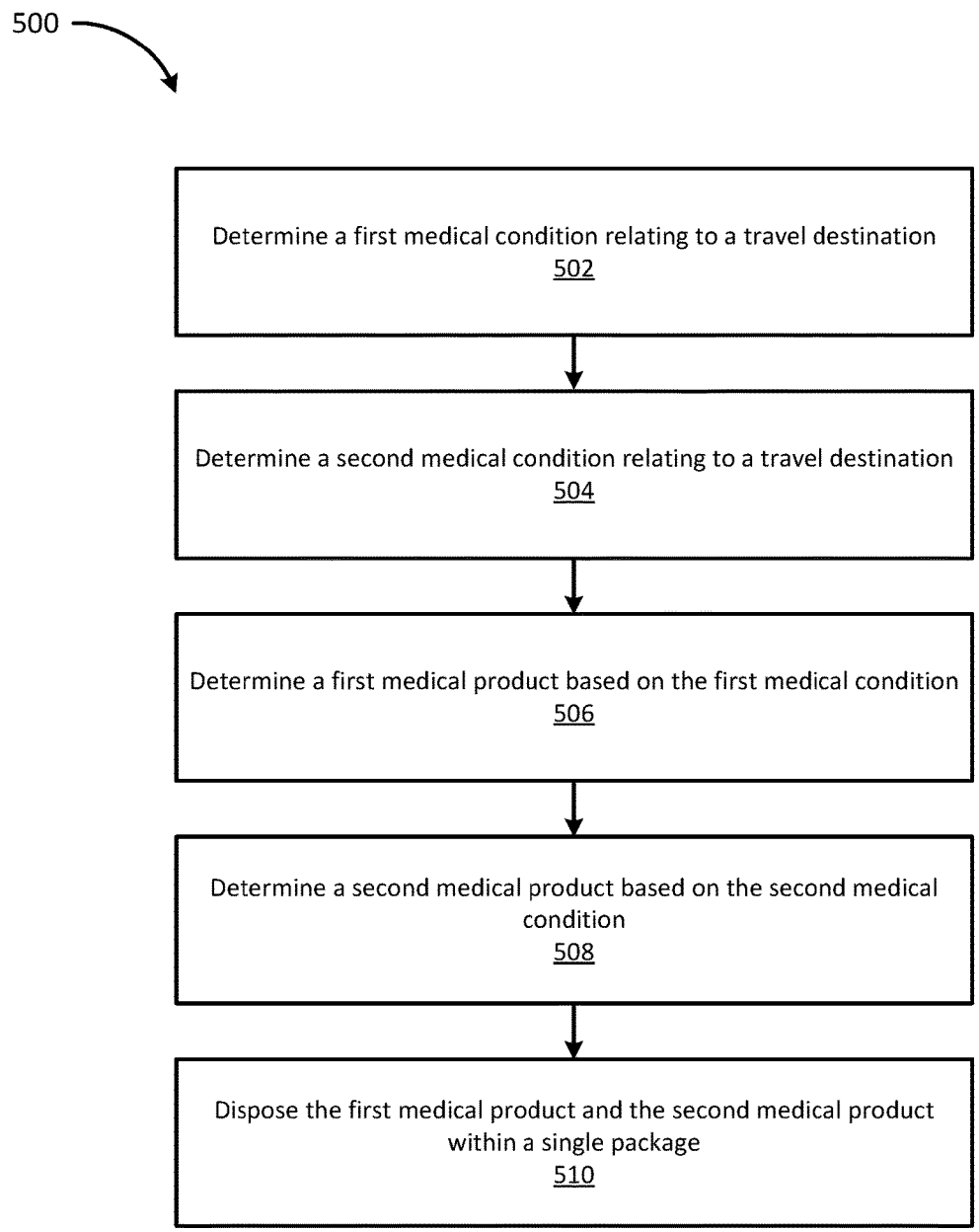
FIG. 5 illustrates a method of making a travel package for medications or other medical products.

FIG. 5 depicts a method 500 for assembling a travel package containing medical products for use while a patient visits a travel destination. At step 502, a first medical condition relating to the travel destination may be determined. At step 504, a second medical condition relating to the travel destination may be determined. A medical condition may include an illness, a disease, an injury, or a medical symptom. The first and second medical conditions may each include a medical condition that the patient is more likely to suffer from at the travel destination than at the patient's home locale. The first and second medical conditions may each be determined based, at least, on one or more factors associated with the travel destination, such as an infrastructure factor, an environmental factor, a flora/fauna factor, or a common disease factor, as discussed in detail above.

As an example, the patient may intend to take a trip to Panama. The first medical condition may be determined to be dengue fever according to a common disease factor indicating that dengue fever is common in Panama. The second medical condition may be determined to be insect bites based on a flora/fauna factor indicating that there are a high number of biting insects in Panama.

At step 506, a first medical product, such as the first medical product 116, may be determined based, at least, on the first medical condition of step 502. At step 508, a second medical product, such as the second medical product 118, may be determined based, at least, on the second medical condition of step 504. The first and second medical products may be medical products that may treat or otherwise address the first and second medical conditions, respectively, or symptom thereof. The first medical product and/or the second medical product may further be determined based on an age, weight, and/or gender of the patient. The packaging and associated medical products may be configured for an individual, a family, or a group of individuals traveling together.

Continuing the Panama trip example, the first medical product may be a medical product that alleviates the symptoms of dengue fever, the first medical condition. Accordingly, the first medical product may be acetaminophen pills for managing the fever and pain caused by the dengue fever. The second medical product may be a medical product for treating insect bites, the second medical condition. Therefore, the second medical product may be diphenhydramine (e.g., Benadryl®) pills to reduce the itching of the insect bites.

At step 508, the first medical product of step 506 and the second medical product of step 508 may be packaged within a single package, such as the package 100, the package 300, or the package 400. As depicted in FIG. 1, the package 100 may be embodied as a blister package. In other embodiments, the package 100 may comprise a box, casing, clamshell, carton, shrink wrap, or formed plastic package. The first medical product may be secured in a first set of one or more sealed blister cavities, such as those included in the first region 106 of the package 100. The second medical product may be secured in a second set of one or more sealed blister cavities, such as those included in the second region 108 of the package 100. Each of the medical products may be secured with its own seal such that the medical products cannot be mixed or confused and configured such that only an individual seal is broken each time a single medical product is accessed. As such, the number and types of medical products consumed can be controlled and audited.

The number of pills or other measure of dosage of the first and second medical products disposed within the package 100 may be determined according to an intended length of time of the trip to the travel destination. Additionally or alternatively, the package 100 may include an amount of the first and second medical products needed or anticipated to be needed for a certain period of time (e.g., a day, a week, etc.). Additionally or alternatively, multiple packages 100 may be provided to a patient may, the number of which may depend upon the total intended length of the trip. For example, if a patient is planning to spend four weeks at the travel destination, the patient may be provided 28 daily packages 100 or 4 weekly packages 100.

Continuing the Panama trip example, the acetaminophen pills (i.e., the first medical product) and the diphenhydramine pills (i.e., the second medical product) may be included in a single blister package. The acetaminophen pills may be situated in a first region of the blister package and the diphenhydramine pills may be situated in a second region of the blister package. The single blister package may be taken by the patient on the patient's trip to Panama, thus providing a single medication package that the patient need pack and keep track of.

One or more or steps of the method 500 may be performed by one or more of a physician or other medical care provider, a pharmacist, or a third party (i.e., a party other than a physician or pharmacist), such as a drug manufacturer. For example, a physician may determine the medical conditions that the patient may suffer from while at the travel destination and determine the medical products appropriate to address those medical conditions. The physician may possess a means for packaging and may accordingly package the determined medical products in a single package. In an aspect, a pharmacist may receive an indication of the medical products determined by the physician and the pharmacist may produce the package including the medical products.

As another example, a third party, such as a drug manufacturer, may determine the medical conditions that an individual (i.e., not a specific patient) may experience while visiting a particular travel destination and determine the medical products that may address those medical conditions. The third party may package the determined medical products in single packages and distribute the single packages to physicians, pharmacists, retailers, etc., for later distribution to patients. In other words, the packages may be pre-packed by the third party according to travel destination or the other factors mentioned herein. A physician, for example, may provide or prescribe a pre-packaged package for India to a patient that is planning a trip to India.

In some aspects, a travel destination may be defined according to a geographical region (not to be confused with the various regions described in relation to the package 100, 300, and 400 of FIGS. 1, 3, and 4, respectively). A geographical region, in turn, may be defined according to one or more common attributes. It is generally contemplated that the portions of a geographical region be substantially contiguous with one another. That is, another geographical region or unclassified space is not interposed between the portions of the instant geographical region.

Thus, in one aspect, the determination of the first and/or second medical products discussed in relation to the method 500 of FIG. 5 and/or the method 600 of FIG. 6 (discussed below) may be based on the geographical region defining the travel destination. In another aspect, the first and/or second medical conditions, also discussed in relation to the method 500, may be determined based on the geographical region defining the travel destination. In such case, the determination of the first and/or second medical products may be indirectly affected by the geographical region.

One attribute that may define a geographical region may be a political boundary. In other words, the areas within a particular political boundary make up the geographical region. A political boundary may be demarcated at various levels of a hierarchy. Such hierarchy may include a country, a state (including a province, an administrative region, or other direct subdivision of a country), a county (including other direct subdivisions of a state), and a city (including those designated as a town, village, etc.). For example, an attribute of a region defined by a political boundary may have an attribute of at least one of the United States, the state of Florida, Miami-Dade county, or the city of Miami. Although not strictly delineated by a political boundary, a continent also may be considered as bounding a region.

Another common attribute defining a geographical region may be one or more common physical and naturally-occurring geographical features, which also may include landmasses. For example, a geographical feature may include a singular or range of mountains (e.g., Mount Everest or the Andes), an inland body of water (e.g., the Nile river), a desert (e.g., the Gobi desert), a peninsula (e.g. the Iberian peninsula), an island, a plateau, a canyon, a valley, a shoreline, a volcano, or a glacier. The corresponding area surrounding or near the geographic feature may be included within the geographical region according to the understanding of one skilled in the art. For example, a flood plain or banks of a river may be considered as within the geographical region defined by the river.

Yet another attribute defining a geographical region may be a common ecoregion. An ecoregion may represent an ecologically and geographically defined area. That is, a region defined by a common ecoregion may have a common ecology and be within a common geographical boundary. One example of an ecoregion may be the East Siberian taiga located substantially with Russia. It is noted that the bounds of the East Siberian taiga are unrelated to the political boundary of Russia. Another example of an ecoregion may be the Piedmont ecoregion spanning, in part, over the U.S. states of Georgia, South Carolina, North Carolina, and Virginia. Again, the area identified as belong to to the Piedmont region is independent of the political boundaries of the states.

An attribute defining a geographical region also may be a shared climate. For example, a subarctic climate may be common to the northern portions of Scandinavia and Russia. As another example, the northern portions of Africa, roughly corresponding to the Sahara desert, share an arid climate. A climate may be classified according to the Koppen climate classification system. Relating to the climate attribute, another attribute that may define a geographical region may be a common geographical latitude. For example, areas across a continent at the same latitude tend to have common characteristics, particularly with respect to conditions that might affect a traveler's medical condition. A common latitude may be defined as latitudes that are within 3° degrees of a baseline latitude.

Another attribute that may define a geographical region is population density, such as the number of people per square mile. A population density may tend to delineate a city region from a rural or suburban region. For example, New York City, with its high population density, may be distinguished from upstate New York, which has a relatively lower population density. A common population density may be defined as those areas which vary by 10% or less from a baseline population density. For example, if a baseline population density is 10,000 people per square mile, areas with a common population density attribute include those areas with a population density between 9,000 people per square mile and 11,000 people per square mile.

It will be appreciated that some of the attributes by which a region is defined may be interrelated with one another. For example, the delineations of an ecoregion may be affected, in part, by the climate of that area. As another example, a type of landmass may affect the climate of an area. For instance, the high altitude of a mountain range may tend to cause lower temperatures. Further, a geographical region may be defined by two or more attributes. That is, areas that share all of the two or more attributes define the region. For example, a region may be defined by an attribute specifying the Unites States and another attribute specifying the Rocky Mountains. The region defined by these attributes would include the areas of the Rocky Mountains between New Mexico and Montana, but excluding the Rocky Mountain areas within Canada.

In some aspects, the medical product(s) that are stored and carried in the package 100, 300, and 400 of FIGS. 1, 3, and 4, respectively, may be selected from one or more classes of medical products. For example, one medical product of a package may belong to one class of medical product and a second medical product of the package may belong to a second, different class of medical product. Such classes of medical products may include anti-allergy, anti-diarrhea, anti-emetic, anti-spasmodic, antibiotic, antiviral, anti-parasitic anti-fungal, non-steroidal pain reliever, narcotic pain reliever, anti-anxiety, hypnotic, antitussive, antacid, and anti-motion sickness.

In an aspect, the geographical region may be defined as the region of Mainland Southeast Asia (i.e., Indochina) comprising the countries of Vietnam, Laos, Cambodia, Thailand, Myanmar, and Malaysia, wherein each of the aforementioned countries may further define a geographical region.

In an aspect, the geographical region may be defined as the region of Maritime Southeast Asia (i.e., the East Indies) comprising the countries of Indonesia, Malaysia, Singapore, Philippines, East Timor, Brunei, Christmas Island, Andaman and Nicobar Islands, and Cocos (Keeling) Islands, wherein each of the aforementioned countries may further define a geographical region.

In an aspect, the geographical region may be defined as the region of South Asia comprising the countries of Bangladesh, India, Pakistan, Afghanistan, Nepal, Bhutan, Sri Lanka, and Maldives, wherein each of the aforementioned countries may further define a geographical region.

In an aspect, the geographical region may be defined as the region of East Asia comprising the countries of China, Mongolia, North Korea, South Korea, Japan, and Taiwan, wherein each of the aforementioned countries may further define a geographical region.

In an aspect, the geographical region may be defined as the region of Central Asia comprising the countries of Kazakhstan, Kyrgyzstan, Tajikistan, Turkmenistan, Uzbekistan, and Afghanistan, wherein each of the aforementioned countries may further define a geographical region.

In an aspect, the geographical region may be defined as the region of Western Asia comprising the countries of Bahrain, Iran, Iraq, Israel, Jordan, Kuwait, Lebanon, Oman, Qatar, Palestinian territories, Saudi Arabia, Syria, Turkey, U A E, and Yemen, wherein each of the aforementioned countries may further define a geographical region.

In an aspect, the geographical region may be defined as the region of North Asia comprising the country of Russia, wherein the aforementioned country may further define a geographical region.

In an aspect, the geographical region may be defined as the region of Southern Europe comprising the countries of Spain, Portugal, Greece, Italy, and Malta, wherein each of the aforementioned countries may further define a geographical region.

In an aspect, the geographical region may be defined as the region of Western Europe comprising the countries of Belgium, France, Ireland, Luxembourg, Monaco, the Netherlands, Switzerland, Spain, Portugal, Germany, and the United Kingdom, wherein each of the aforementioned countries may further define a geographical region.

In an aspect, the geographical region may be defined as the region of Northern Europe comprising the countries of Iceland, the Republic of Ireland, the Isle of Man, the United Kingdom, the Faroe Islands, the Netherlands, Germany, Denmark, Norway, Sweden, Finland, Estonia, Latvia, Lithuania, and Belarus, wherein each of the aforementioned countries may further define a geographical region.

In an aspect, the geographical region may be defined as the region of Eastern Europe comprising the countries of Belarus, Bulgaria, Greece, Republic of Macedonia, Moldova, Montenegro, Romania, Russia, Serbia, Ukraine, Estonia, Latvia, Lithuania, Georgia, Armenia, Azerbaijan, Albania, Bosnia and Herzegovina, Austria, Czech Republic, Croatia, Hungary, Poland, and Slovakia, wherein each of the aforementioned countries may further define a geographical region.

In an aspect, the geographical region may be defined as the region of Central Europe comprising the countries of Austria, Croatia, Czech Republic, Germany, Hungary, Liechtenstein, Poland, Slovakia, Slovenia, and Switzerland, wherein each of the aforementioned countries may further define a geographical region.

In an aspect, the geographical region may be defined as the region of Northern America comprising the countries of Canada, Greenland, Saint Pierre and Miquelon, Mexico, and the United States, wherein each of the aforementioned countries may further define a geographical region.

In an aspect, the geographical region may be defined as the region of Central America comprising the countries of Belize, Costa Rica, El Salvador, Guatemala, Honduras, Nicaragua, and Panama, wherein each of the aforementioned countries may further define a geographical region.

In an aspect, the geographical region may be defined as the region of South America comprising the countries of Argentina, Bolivia, Brazil, Chile, Colombia, Ecuador, Guyana, Paraguay, Peru, Suriname, Uruguay, and Venezuela, wherein each of the aforementioned countries may further define a geographical region.

In an aspect, the geographical region may be defined as the region of the Caribbean comprising the countries of Anguilla, Antigua and Barbuda, Aruba, Bahamas, Barbados, British Virgin Islands, Cayman Islands, Cuba, Curacao, Dominica, Dominican Republic, Grenada, Guadeloupe, Haiti, Jamaica, Martinique, Montserrat, Navassa Island, Puerto Rico, Saint-Barthelemy, Saint Kitts and Nevis, Saint Lucia, Saint Martin, Saint Vincent and the Grenadines, Trinidad and Tobago, Turks and Caicos Islands, and the United States Virgin Islands, wherein each of the aforementioned countries may further define a geographical region.

In an aspect, the geographical region may be defined as the region of Antarctica.

In an aspect, the geographical region may be defined as the region of Oceania comprising the countries of Australia, New Guinea, New Zealand, Melanesia, Micronesia, and Polynesia, wherein each of the aforementioned countries may further define a geographical region.

In an aspect, the geographical region may be defined as the region of North Africa comprising the countries of Morocco, Algeria, Tunisia, Libya, Egypt, and Sudan, wherein each of the aforementioned countries may further define a geographical region.

In an aspect, the geographical region may be defined as the region of East Africa comprising the countries of Tanzania, Kenya, Uganda, Rwanda, Burundi, South Sudan, Djibouti, Eritrea, Ethiopia, Somalia, Comoros, Mauritius, Seychelles, Mozambique, Madagascar, Malawi, Zambia, and Zimbabwe, wherein each of the aforementioned countries may further define a geographical region.

In an aspect, the geographical region may be defined as the region of Central Africa comprising the countries of Burundi, the Central African Republic, Chad, the Democratic Republic of the Congo, and Rwanda, wherein each of the aforementioned countries may further define a geographical region.

In an aspect, the geographical region may be defined as the region of West Africa comprising the countries of Benin, Burkina Faso, Cape Verde, Gambia, Ghana, Guinea, Guinea-Bissau, Ivory Coast, Liberia, Mali, Mauritania, Niger, Nigeria, Saint Helena, Senegal, Sierra Leone, Sao Tome, Principe, and Togo, wherein each of the aforementioned countries may further define a geographical region.

In an aspect, the geographical region may be defined as the region of South Africa comprising the countries of Angola, Botswana, Lesotho, Malawi, Mozambique, Namibia, South Africa, Swaziland, Zambia, and Zimbabwe, wherein each of the aforementioned countries may further define a geographical region.

Figure 6:
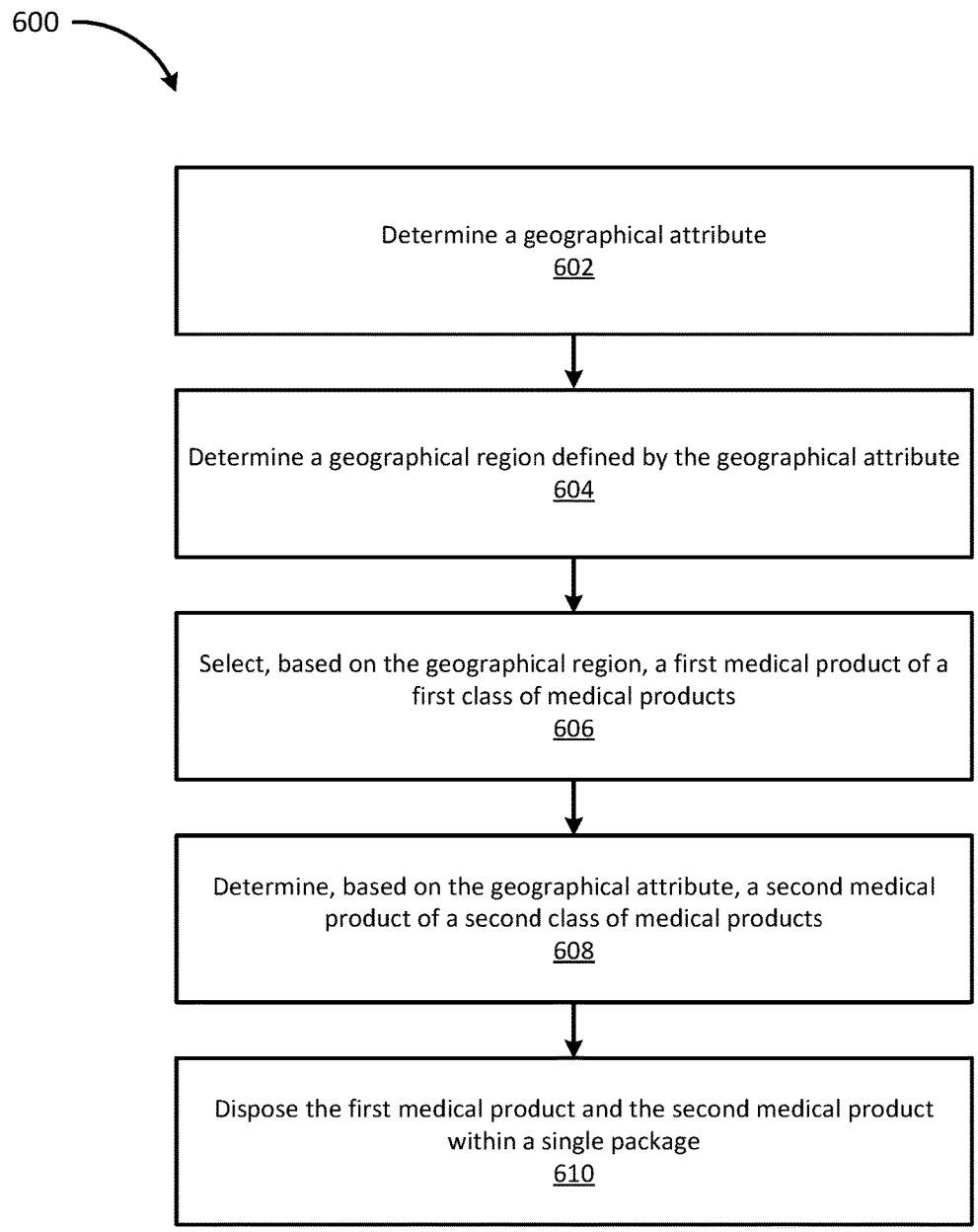
FIG. 6 illustrates a method of making a travel package for medication or other medical products.

FIG. 6 illustrates a method for assembling a travel package based on a patient's travel destination. At step 602, one or more geographical attributes may be determined that relate to geographic regions. As noted above, an attribute may relate to political boundary, ecoregion, climate, latitude, geographic features, and/or population density. At step 604, a geographical region may be determined that is defined by the one or more geographical attributes. For example, the geographical region may have the geographical attribute in common. As another example, the geographical region may have both a first geographical attribute and a second geographical attribute in common.

At step 606, based on the geographical region, a first medical product may be selected, wherein the first medical product belongs to a first class of medical products. As described above, a class of medical products may include anti-allergy, anti-diarrhea, anti-emetic, anti-spasmodic, anti-biotic, antiviral, anti-parasitic anti-fungal, non-steroidal pain reliever, narcotic pain reliever, anti-anxiety, hypnotic, anti-tussive, antacid, anti-motion sickness. In an aspect, the first class of medical product itself may be first determined based on the geographical region. For example, it may be determined that an anti-diarrhea medication may be needed at the geographical region. Then, a particular anti-diarrhea medication may be selected from the numerous medications in the anti-diarrhea class. The selection of the medication from the class may be based on the geographical region or not based on the geographical region. For example, the class may be determined based on the geographical region, but the particular medication selected from that class may be based on other factors, such as the individual characteristics of the patient (e.g., drug allergies, interactions with current medications, or age).

At step 608, based on the geographical region, a second medical product may be selected, with the second medical product belonging to a second class of medical products that is different from the first class of medical products. For example, the first medical product may be an antihistamine (an anti-allergy medication) and the second medical product may be penicillin (an antibiotic). In some aspects, the selection of the first and/or second medical products may be based on the geographical attribute in addition to and instead of the geographical region. Similar to step 608, the second class of medical product may be first determined based on the geographical region. Then, the particular medical product may be selected from that class.

At step 610, the first medical product and the second medical products may be disposed within a single package, such as the package 100, the package 300, or the package 400 of FIGS. 1, 3, and 4, respectively. For example, the first medical product may be secured within a first region of cavities in a blister package and the second medical product may be secured with a second region of cavities in the blister package.

In some aspects, the techniques described herein, including the method 500 of FIG. 5 and the method 600 of FIG. 6, may be performed, at least in part, by a computer system. In this implementation, a user (e.g., a physician or pharmacist) may enter into the computer system one or more of the parameters described herein that may affect the determination of the medical products carried in a travel package. The user may enter, for example, the travel destination to which the patient intends to visit. The user also may enter one or more medical conditions that the user suspects may inflict the patient. Yet further, the user may enter one or more factors relating to the travel destination, such as the infrastructure factor, environmental factor, flora/fauna factor, travel factor, or common disease factor described above. The user may also enter into the computer system other parameters that may affect which medical products should be included in the travel package. For example, a parameter may include the medical history, age, weight, gender, or ongoing medical conditions of the patient. Other parameters that the user may enter into the computer system may include one or more geographical attributes that may define a geographical region to which the patent intents to travel.

Based on these inputs entered into the computer system, logic implemented by the computer system may determine one or more of the medical products to be carried in the package. As another example, the logic may first determine a geographical region based on the geographical attributes input to the computer system. The logic, in turn, may determine the medical products based on the geographical region.

For example, the computer system may store or access one or more tables relating to the various parameters, geographical regions, medical products, etc. described herein. The medical products to be included in the travel package may be determined according to a one or more cross-references between the tables.

Figure 7:
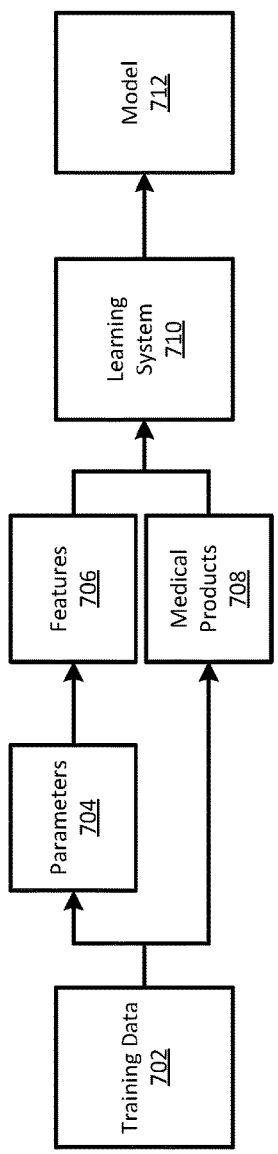
FIG. 7 illustrates a data flow diagram relating to a machine learning training system.

In one aspect, the determination of the medical product may be effectuated by machine learning techniques. FIG. 7 illustrates an example data flow diagram 700 relating to a training system that applies machine learning techniques to determine a resultant model 712. The model 712 later may be used to determine one or more medical products based on a user input. The training system may be realized in a computer system, including a centralized computer such as a server.

The training system may receive a set of training data 702, which may form the basis from which the model 712 may be formed. The training data 702 may be received as a single set or may be received cumulatively over time. The training data 702 may embody a series of input parameters and a series of output medical products (or more accurately, the identifications of those medical products).

The training data 702 may be analyzed to extract parameters 704 and resultant medical products 708 based on those parameters 704. The parameters 704 may be input by a user and may include any of the various parameters described herein, such as a travel destination, a medical condition, a geographical attribute, or a geographical region. The parameters 704 may further include other data by which a medical product may be determined, such as patient medical history, age, gender, or weight. Each of the parameters 704 (or multiple parameters if used together to determine a medical product) may be correlated to one or more medical products 708 that were determined based on that parameter 704. For example, a correlated pair of a parameter and resultant medical product may be the result of a user input of the parameter and a subsequent indication of the medical product by the user. Such may be the case if a physician uses a computer system to input the parameter, determines the medical product, and then inputs the determined medical product in the computer system. That correlated pair of the input parameter and resultant medical product may be stored and represented in the training data 702.

Further, the parameters 704 may be analyzed to determine one or more features 706 of each of the parameter. The features may comprise a characteristic, factor, attribute, or the like that is associated with the parameter. For example, a travel destination parameter may be associated with one or more of the travel destination factors or other characteristics described herein. As an example, a parameter identifying Vietnam as a travel destination may be analyzed to determine the associated features: Southeast Asia as a continental region characteristic, humid as a weather characteristic, Indochina Peninsula as a landmass characteristic, venomous snakes as a fauna characteristic, and 714.9 persons per square mile as a population density characteristic. The features 706 may be determined based on a separate database or index of potential parameters (e.g., a travel destination or geographical region) and features corresponding to that parameter. In addition, the features 706 may be determined by user input, such as user input provided in conjunction with the user input of the parameter 704. The features 706 may be correlated with one or more of the medical products 708. In particular, the features 706 may be correlated with the same medical products 708 as the parameter 704 upon which the features 706 are based.

The correlated medical products 708 and parameters 704 and/or features 706 may be provided to the learning system 710. Specifically, the sets of correlated parameters 704 and/or features 706 and resultant medical products 708 may be provided to the learning system 710, with the parameters 704 and/or features 706 of each correlated set being an input object and the medical products 708 of the set being a corresponding output object. Via one or more machine learning algorithms, such as supervised learning, decision tree learning, Bayesian networks, or artificial neural networks, the learning system 710 may determine the model 712.

The model 712 may represent the collective correlations of the parameters 704 and/or features 706 and the respective resultant medical products 708. With an input of new parameter(s) and/or feature(s) relating to a geographical region, travel destination, etc., the model 712 may be used to determine one or more medical products based on that input.

Figure 8:
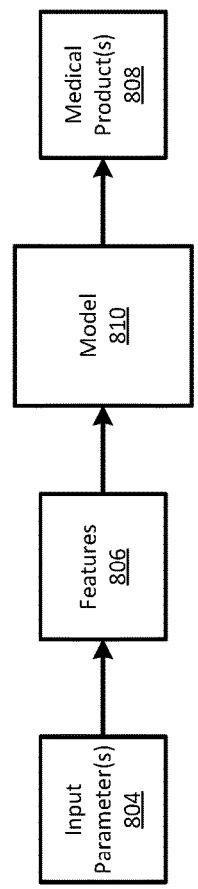
FIG. 8 illustrates a data flow diagram relating to a use of a model from a machine learning training system.

FIG. 8 illustrates a data flow diagram 800 in which a model 810 is used to determine one or more medical products 808. Initially, one or more parameters 804 may be received. For example, the parameter 804 may be received in a computer system from a user input, such as a user input from a physician. The parameter 804 may be analogous to the parameters 704 described in relation to FIG. 7. The parameter 804 may be analyzed to determine one or more features 806 associated with the parameter 804. The features 806 may be likewise analogous to the features 706 of FIG. 7. The features 806 and/or the parameter 804 may be input to the model 810. Based on this input, the model 810 may determine one or more medical products 808. The medical products 808 may be then included in the travel package.

The methods as systems described herein may be at least partially implemented as computer-executable instructions. Such instructions may be stored or distributed on computer-readable media, such as a memory, including magnetic and optically readable and removable computer disks, hard-wired or preprogrammed in chips (e.g., EEPROM semiconductor chips or ASICs), as well as distributed electronically over the Internet or over other networks (including wireless networks). Computer readable storage media disclosed herein does not include signals.

Figure 9:
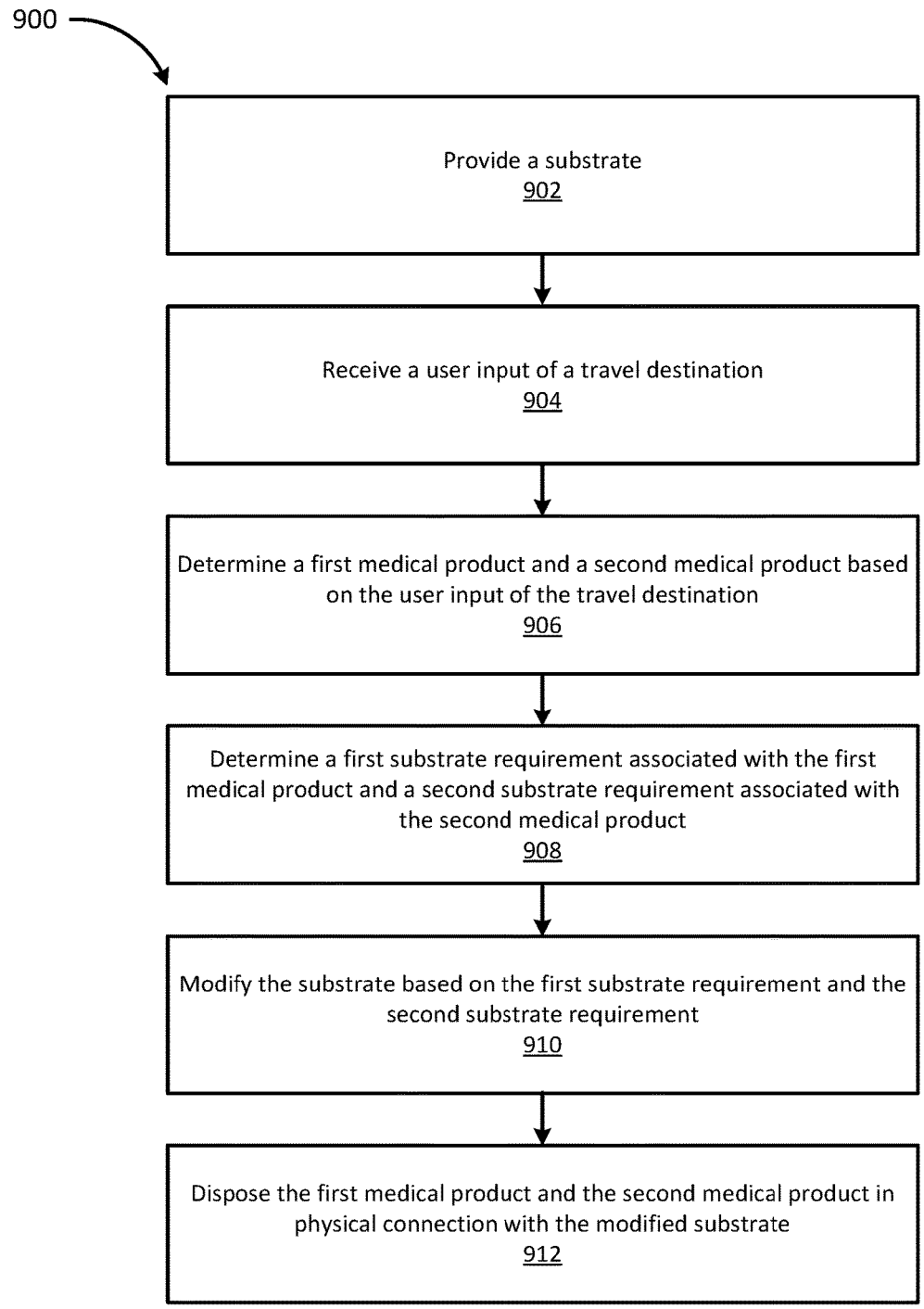
FIG. 9 illustrates a method of making a travel package for medication or other medical products.

FIG. 9 illustrates a method 900 relating to the assembly of a travel medication package. At step 902, a substrate is provided, such as the substrate 102, the substrate 302, or the perforated sheet 402 of FIGS. 1, 3, and 4, respectively. At step 904, a user input of a travel destination may be received. The user input may be received via a computer system. The travel destination may be defined as a geographical region having a common attribute. At step 906, a first medical product and a second medical product may be determined based on the user input of the travel destination. The first and second medical products may be determined according to any such method described herein.

At step 908, a first substrate requirement associated with the first medical product and/or a second substrate requirement associated with the second medical product each may be determined. As an example, a substrate requirement may comprise a number of cavities to accommodate each pill for a full dose of the medical product. The substrate requirement may comprise a size and/or shape of each of the cavities that are appropriate for the medical product(s). The substrate requirement may comprise an arrangement of the cavities, particularly with respect the relative arrangement of the cavities associated with the first medical product and those associated with the second medical product. Another substrate requirement may comprise a visual aspect of the substrate, including an identifier of the medical product, a color of the substrate associated with the medical product, an indicator of the class of medical product to which the medical product belongs, an indicator of a safety warning associated with the medical product, dosage information relating to the medical product, or contact information associated with the medical product. The above visual aspects may be represented by text. Yet another substrate requirement may comprise an aspect relating to the seal of the cavities, such as a sterile seal, a watertight seal, a foil seal, or a puncture-able seal. Another substrate requirement may comprise a type of substrate, such as a blister pack substrate or a perforated sheet substrate.

At step 910, the substrate may be modified based on the first substrate requirement and/or the second substrate requirement. For example, any of the aforementioned example substrate requirements may be effectuated with respect to the substrate. For example, if the substrate requirement indicates that a particular number of cavities are needed for a medical product, the substrate may be configured with at least that many cavities.

At step 912, the first medical product and the second medical product may be disposed in physical connection with the modified substrate. For example, the first and second medical products may each be disposed in one or more cavities of the substrate. As another example, the first and second medical products may be disposed in one or more packets defined by one or more perforated edges of a perforated sheet.

Figure 10:
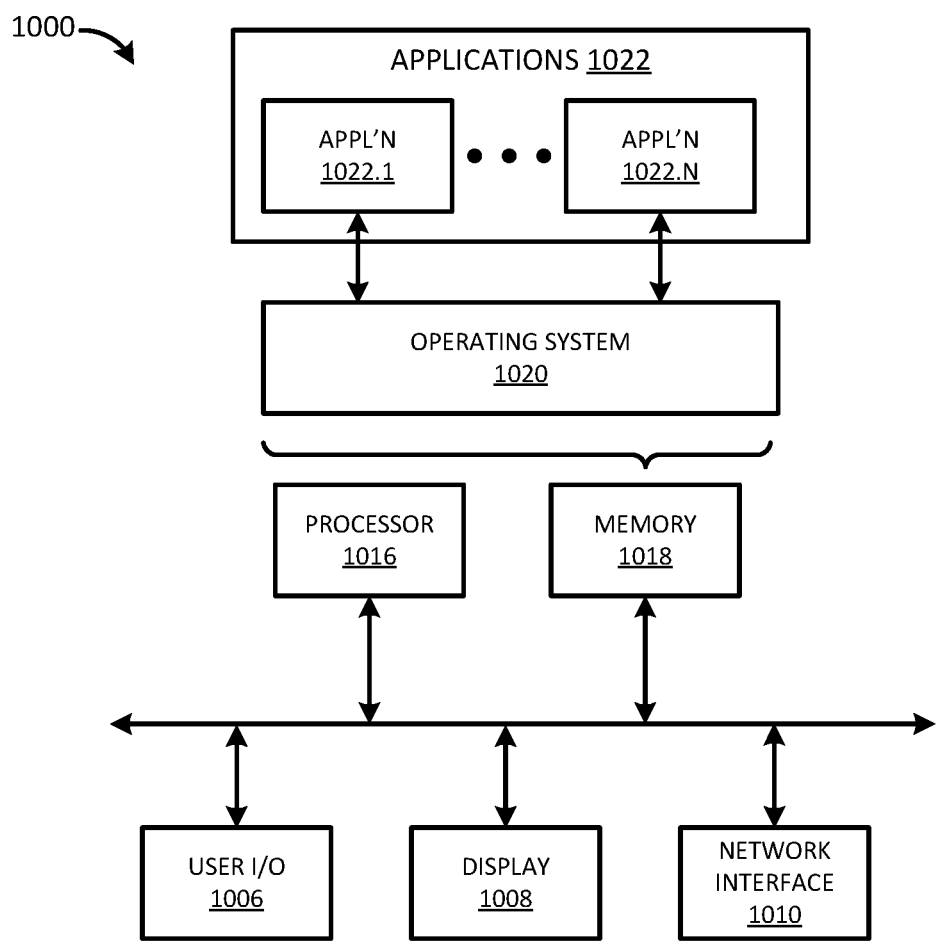
FIG. 10 illustrates a schematic diagram of an example computing system.

FIG. 10 is a block diagram of a computing device 1000 according to an embodiment of the present disclosure. The computing device 1000 may implement any of the systems, components, and methods of the present disclosure, including, but not limited to the methods 500, 600, and 900 of FIGS. 5, 6, and 9 and the data flow diagrams 700 and 800 of FIGS. 7 and 8. It is contemplated that multiple computing devices 1000 may act in conjunction to implement any of the systems or methods described herein.

The computing device 1000 may include a processor 1016 and a memory 1018. The memory 1018 may store instructions that, when executed by the processor 1016, effectuate any of the methods and techniques described herein. Further, the memory 1018 may store program instructions that define an operating system 1020 and various applications 1022 that are executed by the processor 1016. The applications 1022 may include a number of applications 1022.1-1022.N. The applications 1022 may effectuate the methods 500, 600, and 900 of FIGS. 5, 6, and 9 and the data flow diagrams 700 and 800 of FIGS. 7 and 8. The memory 1018 may also store application data for any of the applications 1022.

The computing device 1000 also includes other components that may be common to computing devices used to implement the systems and methods described herein. Such components may include a user input/output 1006, a display 1008, and a network interface 1010.

The user input/output 1006 may be realized as a pointing device, a keyboard, or a touch-sensitive display, and the like to enable a user to interact with the computing device 1000. The display 1008 may render video output, such as encoded video data. The network interface 1010 may effectuate communication with other computing devices and/or similar systems. For example, the network interface 1010 may comprise a wired interface (e.g., an Ethernet interface) to effectuate communication over a wired communication channel. As another example, the network interface 1010 may comprise a wireless interface, such as a radio transceiver, to effectuate communication over a wireless communication channel. Such a wireless communication channel may include a cellular network or a Wi-Fi network.

While the disclosure has been described in connection with the various embodiments of the various figures, it is to be understood that other similar embodiments can be used or modifications and additions can be made to the described embodiments. Therefore, the travel packaging for medications as described herein should not be limited to any single embodiment, but rather should be construed in breadth and scope in accordance with the appended claims. Further, the methods and techniques described herein are not limited in execution to the relative ordering presented herein, but may be executed in any relative order.

What is claimed:

1. A medication package comprising:
   a first cavity;
   a second cavity physically connected to the first cavity;
   a first medication sealed in the first cavity;
   a second medication sealed in the second cavity; and
   a scannable indicia associated with the first medication, wherein the scannable indicia is configured to, when scanned by a device, cause the device to transmit, to a computer system accessible by a medical provider, a record indicating that the first medication was accessed from the medication package and enable a virtual consultation with the medical provider based on the transmitted record, wherein:
      a seal of the first cavity must be broken to access the first medication and a seal of the second cavity must be broken to access the second medication,
      the first medication is selected, based on a geographic region, from a first plurality of medications, wherein each medication of the first plurality of medications belongs to a first class of medications selected from the group consisting of: anti-allergy, anti-diarrhea, anti-emetic, anti-spasmodic, antibiotic, antiviral, anti-parasitic, anti-fungal, non-steroidal pain reliever, narcotic pain reliever, anti-anxiety, hypnotic, antitussive, antacid, and anti-motion sickness; and
      the second medication is selected, based on the geographic region, from a second plurality of medications, wherein each medication of the second plurality of medications belongs to a second class of medications, different from the first class of medications, selected from the group consisting of: anti-allergy, anti-diarrhea, anti-emetic, anti-spasmodic, antibiotic, antiviral, anti-parasitic, anti-fungal, non-steroidal pain reliever, narcotic pain reliever, anti-anxiety, hypnotic, antitussive, antacid, and anti-motion sickness.

2. A method of assembling a medication package, the method comprising:
   determining a geographic region;
   determining a first medication based on the geographical region, wherein the first medication is selected from a first plurality of medications, and wherein each medication of the first plurality of medications belongs to a first class of medications selected from the group consisting of: anti-allergy, anti-diarrhea, anti-emetic, anti-spasmodic, antibiotic, antiviral, anti-parasitic, anti-fungal, non-steroidal pain reliever, narcotic pain reliever, anti-anxiety, hypnotic, antitussive, antacid, and anti-motion sickness;
   determining a second medication based on the geographical region, wherein the second medication is selected from a second plurality of medications, and wherein each medication of the second plurality of medications belongs to a second class of medications selected from the group consisting of: anti-allergy, anti-diarrhea, anti-emetic, anti-spasmodic, antibiotic, antiviral, anti-parasitic, anti-fungal, non-steroidal pain reliever, narcotic pain reliever, anti-anxiety, hypnotic, antitussive, antacid, and anti-motion sickness;
   disposing the first medication within a first cavity of the medication package;
   disposing the second medication within a second cavity of the medication package, wherein the first cavity and the second cavity are connected to one another via, at the least, the medication package; and configuring the medication package with a scannable indicia associated with the first medication, wherein the scannable indicia is configured to, when scanned by a device, cause the device to transmit, to a computer system accessible by a medical provider, a record indicating that the first medication was accessed from the first cavity and enable a virtual consultation with the medical provider based on the transmitted record.

3. The method of claim 2, wherein determining the first medication is further based on a user and wherein determining the second medication is further based on the user.

4. The method of claim 3, wherein determining the first medication is further based on a first attribute of the user and wherein determining the second medication is further based on a second attribute of the user.

5. The method of claim 2, wherein determining the geographic region is performed by a medical provider, wherein determining the first medication is performed by the medical provider and further based on a request from a user to the medical provider, and wherein determining the second medication is performed by the medical provider and further based on the request from the user to the medical provider.

6. The method of claim 2, further comprising:
configuring the medication package with a second scannable indicia associated with the second medication, wherein the second scannable indicia is configured to, when scanned by the device, cause the device to transmit, to the computer system, a second record indicating that the second medication was accessed from the second cavity, and wherein the virtual consultation with the medical provider is further based on the transmitted second record.

7. The method of claim 2, wherein the virtual consultation with the medical provider is performed via a website.

8. The method of claim 7, further comprising:
configuring the medication package with a website address associated with the website.

9. The method of claim 2, wherein the scannable indicia is further configured to, when scanned by the device, cause the device to store the record on the device.

10. A method comprising:
providing a substrate;
receiving a travel destination;
determining a first medical product based on the travel destination;
determining a second medical product based on the travel destination;
determining a substrate requirement associated with at least one of the first medical product and the second medical product;
modifying the substrate based on the substrate requirement;
disposing the first medical product in physical connection with the substrate;
disposing the second medical product in physical connection with the substrate; and configuring the substrate with a scannable indicia associated with the first medical product, wherein the scannable indicia is configured to, when scanned by a device, cause the device to transmit, to a computer system accessible by a medical provider, a record indicating that the first medical product was accessed from the substrate and enable a virtual consultation with the medical provider based on the transmitted record.

11. The method of claim 10, wherein the substrate requirement indicates a number of cavities for storing at least one of the first medical product and the second medical product.

12. The method of claim 10, wherein the substrate requirement indicates at least one of:
a size of a cavity for storing at least one of the first medical product and the second medical product, and
a shape of a cavity for storing at least one of the first medical product and the second medical product.

13. The method of claim 10, wherein the substrate requirement indicates at least one of textual information associated with at least one of the first medical product and the second medical product and a relative positioning of the first medical product and the second medical product.

14. The method of claim 10, wherein determining the first medical product is further based on a user and wherein determining the second medical product is further based on the user.

15. The method of claim 14, wherein determining the first medical product is further based on a first attribute of the user and wherein determining the second medical product is further based on a second attribute of the user.

16. The method of claim 10, wherein receiving the travel destination is performed by a medical provider, wherein determining the first medical product is performed by the medical provider and further based on a request from a user to the medical provider, and wherein determining the second medical product is performed by the medical provider and further based on the request from the user to the medical provider.

17. The method of claim 10, further comprising:
configuring the substrate with a second scannable indicia associated with the second medical product, wherein the second scannable indicia is configured to, when scanned by the device, cause the device to transmit, to the computer system, a second record indicating that the second medical product was accessed from the substrate, and wherein the virtual consultation with the medical provider is further based on the transmitted second record.

18. The method of claim 10, wherein the virtual consultation with the medical provider is performed via a website.

19. The method of claim 18, further comprising:
configuring the substrate with a website address associated with the website.

20. The method of claim 10, wherein the scannable indicia is further configured to, when scanned by the device, cause the device to store the record on the device.

* * * * *